(12) United States Patent
Berckmans, III et al.

(10) Patent No.: US 9,204,944 B2
(45) Date of Patent: *Dec. 8, 2015

(54) DEPOSITION OF DISCRETE NANOPARTICLES ON A NANOSTRUCTURED SURFACE OF AN IMPLANT

(71) Applicant: Biomet 3I, LLC, Palm Beach Gardens, FL (US)

(72) Inventors: Bruce Berckmans, III, Palm Beach Gardens, FL (US); Ross W. Towse, Palm City, FL (US); Robert L. Mayfield, Jupiter, FL (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/151,264

(22) Filed: Jan. 9, 2014

(65) Prior Publication Data

US 2014/0127392 A1    May 8, 2014

Related U.S. Application Data

(60) Continuation of application No. 13/110,633, filed on May 18, 2011, now Pat. No. 8,647,118, which is a division of application No. 11/977,351, filed on Oct. 24, 2007, now Pat. No. 7,972,648.

(60) Provisional application No. 60/854,027, filed on Oct. 24, 2006.

(51) Int. Cl.
*B05D 3/12* (2006.01)
*A61K 6/00* (2006.01)

(Continued)

(52) U.S. Cl.
CPC .............. *A61C 13/00* (2013.01); *A61B 17/86* (2013.01); *A61L 27/04* (2013.01); *A61L 27/10* (2013.01);

(Continued)

(58) Field of Classification Search
CPC ....................................................... A61C 13/00
USPC ........................................ 427/2.26, 2.27, 180
See application file for complete search history.

(56) References Cited

U.S. PATENT DOCUMENTS

| 4,746,532 A | 5/1988 | Suzuki et al. |
| 5,030,474 A | 7/1991 | Saita et al. |

(Continued)

FOREIGN PATENT DOCUMENTS

| DE | 3516411 | 11/1986 |
| WO | WO 2006/096793 | 9/2006 |

(Continued)

OTHER PUBLICATIONS

PCT International Search Report for International Application No. PCT/US07/22511 dated Oct. 24, 2007 (4 pages).

(Continued)

*Primary Examiner* — Cachet Sellman
(74) *Attorney, Agent, or Firm* — Nixon Peabody LLP

(57) ABSTRACT

A method of forming an implant to be implanted into living bone is disclosed. The method comprises the act of roughening at least a portion of the implant surface to produce a microscale roughened surface. The method further comprises forming a nanoscale roughened surface on the microscale roughened surface. The method further comprises the act of depositing discrete nanoparticles on the nanoscale roughened surface though a one-step process of exposing the roughened surface to a solution including the nanoparticles. The nanoparticles comprise a material having a property that promotes osseointegration.

19 Claims, 16 Drawing Sheets

(51) Int. Cl.

| | | |
|---|---|---|
| *A61L 27/32* | (2006.01) | |
| *B05D 5/02* | (2006.01) | |
| *A61C 13/00* | (2006.01) | |
| *A61B 17/86* | (2006.01) | |
| *A61L 27/04* | (2006.01) | |
| *A61L 27/10* | (2006.01) | |
| *A61L 27/42* | (2006.01) | |
| *A61L 27/50* | (2006.01) | |
| *B82Y 30/00* | (2011.01) | |
| *C23C 22/02* | (2006.01) | |
| *C23C 24/08* | (2006.01) | |
| *C23C 26/00* | (2006.01) | |
| *C23C 30/00* | (2006.01) | |
| *A61C 8/00* | (2006.01) | |
| *A61F 2/30* | (2006.01) | |

(52) U.S. Cl.
CPC ............... *A61L 27/425* (2013.01); *A61L 27/50* (2013.01); *B82Y 30/00* (2013.01); *C23C 22/02* (2013.01); *C23C 24/08* (2013.01); *C23C 26/00* (2013.01); *C23C 30/00* (2013.01); *A61C 8/0012* (2013.01); *A61C 8/0013* (2013.01); *A61F 2/30767* (2013.01); *A61F 2002/3084* (2013.01); *A61F 2002/30968* (2013.01); *A61F 2310/00796* (2013.01); *A61L 2400/12* (2013.01); *A61L 2430/02* (2013.01); *A61L 2430/12* (2013.01)

(56) References Cited

U.S. PATENT DOCUMENTS

| | | | |
|---|---|---|---|
| 5,128,169 | A | 7/1992 | Saita et al. |
| 5,134,009 | A | 7/1992 | Ichitsuka et al. |
| 5,188,670 | A | 2/1993 | Constantz |
| 5,263,491 | A | 11/1993 | Thornton |
| 5,478,237 | A | 12/1995 | Ishizawa |
| 5,522,893 | A | 6/1996 | Chow et al. |
| 5,726,524 | A | 3/1998 | Debe |
| 5,727,943 | A | 3/1998 | Beaty et al. |
| 5,763,092 | A | 6/1998 | Lee et al. |
| 5,817,326 | A | 10/1998 | Nastasi et al. |
| 5,876,453 | A | 3/1999 | Beaty |
| 5,902,109 | A | 5/1999 | Reams, III et al. |
| 5,934,287 | A | 8/1999 | Hayashi et al. |
| 6,013,591 | A * | 1/2000 | Ying et al. ............ 501/1 |
| 6,051,272 | A | 4/2000 | Stupp et al. |
| 6,069,295 | A | 5/2000 | Leitao |
| 6,143,037 | A | 11/2000 | Goldstein et al. |
| 6,261,322 | B1 | 7/2001 | Despres, III et al. |
| 6,270,347 | B1 | 8/2001 | Webster et al. |
| 6,344,276 | B1 | 2/2002 | Lin et al. |
| 6,372,354 | B1 | 4/2002 | Park et al. |
| 6,518,328 | B2 | 2/2003 | Kumar |
| 6,544,732 | B1 | 4/2003 | Chee et al. |
| 6,569,489 | B1 | 5/2003 | Li |
| 6,582,470 | B1 | 6/2003 | Lee et al. |
| 6,589,590 | B2 | 7/2003 | Czernuszka et al. |
| 6,853,075 | B2 | 2/2005 | Auner et al. |
| 6,919,070 | B1 | 7/2005 | Rudin et al. |
| 6,960,249 | B2 | 11/2005 | Lin et al. |
| 6,969,474 | B2 * | 11/2005 | Beaty ................... 216/109 |
| 6,969,501 | B2 | 11/2005 | Sapieszko et al. |
| 6,991,803 | B2 | 1/2006 | Sapieszko et al. |
| 7,007,872 | B2 | 3/2006 | Yadav et al. |
| 7,018,418 | B2 | 3/2006 | Amrich et al. |
| 7,067,169 | B2 * | 6/2006 | Liu et al. ............. 427/2.13 |
| 7,067,577 | B2 | 6/2006 | Aramaki et al. |
| 7,083,642 | B2 | 8/2006 | Sirhan et al. |
| 7,087,086 | B2 | 8/2006 | Li et al. |
| 7,105,030 | B2 | 9/2006 | Despres, III et al. |
| 7,169,317 | B2 | 1/2007 | Beaty |
| 2002/0016635 | A1 | 2/2002 | Despres, III et al. |
| 2002/0028424 | A1 | 3/2002 | Prestipino et al. |
| 2002/0061494 | A1 | 5/2002 | Klardie et al. |
| 2002/0119325 | A1 | 8/2002 | Park et al. |
| 2003/0082232 | A1 | 5/2003 | Lee et al. |
| 2003/0138473 | A1 | 7/2003 | Koblish et al. |
| 2003/0175773 | A1 | 9/2003 | Chee et al. |
| 2004/0024081 | A1 | 2/2004 | Trieu et al. |
| 2004/0053197 | A1 | 3/2004 | Minevski et al. |
| 2004/0053198 | A1 | 3/2004 | Minevski et al. |
| 2004/0053199 | A1 | 3/2004 | Minevski et al. |
| 2004/0121290 | A1 | 6/2004 | Minevski et al. |
| 2004/0142304 | A1 | 7/2004 | Cottrell |
| 2004/0145053 | A1 | 7/2004 | Auner et al. |
| 2004/0149586 | A1 | 8/2004 | Sul |
| 2004/0241613 | A1 | 12/2004 | Jansen et al. |
| 2004/0249472 | A1 | 12/2004 | Liu et al. |
| 2004/0258726 | A1 | 12/2004 | Stupp et al. |
| 2004/0265780 | A1 | 12/2004 | Robb et al. |
| 2005/0019365 | A1 | 1/2005 | Frauchiger et al. |
| 2005/0031704 | A1 | 2/2005 | Ahn |
| 2005/0038498 | A1 | 2/2005 | Dubrow et al. |
| 2005/0100937 | A1 | 5/2005 | Holmes |
| 2005/0211680 | A1 | 9/2005 | Li et al. |
| 2005/0226939 | A1 | 10/2005 | Ramalingam et al. |
| 2005/0249654 | A1 | 11/2005 | Chow |
| 2005/0263491 | A1 | 12/2005 | Beaty |
| 2006/0039951 | A1 | 2/2006 | Sapieszko et al. |
| 2006/0105015 | A1 | 5/2006 | Perla et al. |
| 2006/0110306 | A1 | 5/2006 | Chow et al. |
| 2006/0141002 | A1 | 6/2006 | Liu et al. |
| 2006/0178751 | A1 | 8/2006 | Despres et al. |
| 2006/0219661 | A1 | 10/2006 | Towse et al. |
| 2006/0229715 | A1 | 10/2006 | Istephanous et al. |
| 2006/0246105 | A1 | 11/2006 | Molz et al. |
| 2006/0257358 | A1 | 11/2006 | Wen et al. |
| 2006/0257492 | A1 | 11/2006 | Wen et al. |
| 2007/0010893 | A1 | 1/2007 | Wen et al. |

FOREIGN PATENT DOCUMENTS

| | | |
|---|---|---|
| WO | WO 2006/102347 | 9/2006 |
| WO | WO 2006102347 A2 * | 9/2006 |
| WO | WO 2007/059038 | 5/2007 |

OTHER PUBLICATIONS

PCT Written Opinion for International Application No. PCT/US07/22511 dated Oct. 24, 2007 (8 pages).

Extended European Search Report for EP Application No. 07861488.0 dated Sep. 14, 2012 (10 pages).

T.J. Krinke, K. Deppert, M. H. Magnusson, H. Fissan, Nanostructured Deposition of Nanoparticles from the Gas Phase. vol. 19, 2002 (6 pages).

F. Schulz, S. Franzka, G. Schmild, Nanostructured Surfaces by Deposition of Metal Nanoparticles by Means of Spray Techniques, vol. 12, Advanced Functional Materials, 2002 (5 pages).

Catledge et al., Nanostructured Caramics for Biomedical Implants, Journal of Nanoscience and Nanotechnology (2002) vol. 3(2), pp. 1-20.

Li et al. Hydroxyapatite Coating by Dipping Method and Bone Bonding Strength. vol. 7, Materials Sci. Materials in Med., 1996. (355-357).

Decision on Appeal from the U.S. Patent & Trademark Office in U.S. Appl. No. 09/237,605 dated May 30, 2007.

Request for Rehearing of Decision on Appeal filed by Applicant in U.S. Appl. No. 09/237,605 dated Jul. 30, 2007.

Decision on Request for Rehearing in U.S. Appl. No. 09/237,605 dated Nov. 13, 2007.

Tampieri et al.; "Biologically inspired synthesis of bone-like composite: Self-assembled collagen fibers/hydroxyapatite nanocrystals." J Biomedical Materials Research Part A, vol. 67A, pp. 618-625, 2003.

* cited by examiner

DEPOSITION OF DISCRETE NANOPARTICLES ON A NANOSTRUCTURED SURFACE OF AN IMPLANT

CROSS-REFERENCE TO RELATED APPLICATION

The present application is a continuation of U.S. patent application Ser. No. 13/110,633, filed May 18, 2011, now issued as U.S. Pat. No. 8,647,118, which is a divisional of U.S. patent application Ser. No. 11/977,351, filed Oct. 24, 2007, now issued as U.S. Pat. No. 7,972,648, which claims the benefit of priority of U.S. Provisional Application No. 60/854,027, filed Oct. 24, 2006, all of which are hereby incorporated by reference in their entireties.

FIELD OF THE INVENTION

This invention relates generally to implants and, in particular, to a dental implant having discrete nanocrystalline calcium phosphate particles deposited thereon and methods of making the same.

BACKGROUND OF THE INVENTION

It is becoming more common to replace a missing tooth with a prosthetic tooth that is placed upon and attached to a dental implant. Dental implants are often comprised of metal and metal alloys, including titanium (Ti) and titanium alloys. The dental implant serves as an artificial root that integrates with the gingiva and the bone tissue of the mouth.

For the dental implant to function successfully, sufficient osseointegration is required. In other words, a direct chemical bond between the implant and the bone must be formed and retained. Osseointegration materials may be incorporated onto the surface of the implant to help enhance the osseointegration process. Non-limiting examples of osseointegration materials include calcium phosphate ceramic materials such as hydroxyapatite (HA), which is particularly chemically stable and osseoconductive.

To provide sufficient long-term behavior of an implant having an osseointegration compound on the surface, there must be a sufficient bond strength between the implant and the compound. Moreover, the compound is desirably sufficiently biostable such that the rate of dissolution of the compound is low.

Several existing techniques involve forming a generally thin (e.g., generally less than 10 microns) coating of HA, other calcium phosphates, or other osseointegration compounds for improving the bond strength of the coating to the implant. Plasma spraying and sputtering are two major techniques that have been used to deposit, for example, HA onto an implant. The dissolution rate of HA for these processes, however, may be undesirably high. Moreover, the interface of the HA and the implant is prone to fracture, which is often caused by poor adherence of the HA to the metal implant.

U.S. Pat. App. Pub. No. 2004/0249472 discloses a method of coating an implant with nanoscale calcium phosphate (e.g., HA). Although effective, the disclosed process is hazardous in that it requires utilizing highly flammable chemicals and produces hazardous byproducts (e.g., waste). Moreover, the process is inefficient because it requires that the implant first be coated with a layer comprising alkoxides or tri-functional silanes (i.e., aminopropyltriethoxysilane) to form a positively charged surface of the implant. A second coating layer comprising negatively charged HA nanoparticles is then formed on the first coating layer.

The present invention is directed to an improved implant having discrete nanocrystalline calcium phosphate (e.g., HA) deposited on the implant surface and methods of forming the same.

SUMMARY OF THE INVENTION

The present invention relates to a method of forming an implant to be implanted into living bone. The method comprises the act of roughening at least a portion of the implant surface to produce a microscale roughened surface. The method further comprises the act of forming a nanoscale roughened surface on the microscale roughened surface. The method further comprises the act of depositing discrete nanoparticles on the microscale roughened surface though a one-step process of exposing the nanoscale roughened surface to a solution including the nanoparticles. The nanoparticles comprise a material having a property that promotes osseointegration.

In another aspect, a method of forming a dental implant made of titanium or titanium alloy is disclosed. The method comprises the act of etching at least a threaded bottom portion of the implant to remove a native oxide layer. The method further comprises the act of acid etching the threaded bottom portion to form a roughened surface having a substantially uniform array of microscale irregularities having peak-to-valley heights not greater than about 20 microns. The method further comprises the act of forming nanostructures on the roughened surface. The method further comprises the act of, without pretreating the roughened surface, depositing discrete hydroxyapatite nanocrystals on the roughened surface by exposure to a solution comprising 2-methoxyethanol solvent and the hydroxyapatite nanocrystals.

The invention also discloses a method of forming a nanocrystalline surface on an implant. The method comprises the act of roughening at least a portion of the implant surface to form a roughened surface having microscale irregularities. The method further comprises the act of forming nanostructures on the roughened surface. The method further comprises the act of, without forming an alkoxide on the roughened surface, depositing nanocrystals on the roughened surface. The nanocrystals comprise a material having a property that promotes osseointegration.

According to another embodiment of the present invention, a dental implant is disclosed. The dental implant comprises a head portion having a non-rotational feature. The dental implant further comprises a lowermost end opposing the head portion. The dental implant further comprises a threaded bottom portion for engaging bone between the head portion and the lowermost end. The threaded bottom portion has a roughened surface with a substantially uniform array of microscale irregularities having peak-to-valley heights not greater than about 20 microns. The microscale irregularities further including generally permanent nanostructures formed thereon. The threaded bottom portion further includes discrete nanoparticles located on the roughened surface. The nanoparticles include hydroxyapatite nanocrystals.

According to another embodiment of the present invention, a titanium implant is disclosed. The titanium implant comprises a surface having nanostructures thereon. The titanium implant further comprises hydroxyapatite nanoparticles deposited on the surface.

According to another method of the present invention, a method of forming an implant is disclosed. The method comprises the act of providing a titanium implant. The method further comprises the act of forming nanostructures on a surface of the titanium implant. The method further comprises the act of depositing hydroxyapatite nanoparticles on the surface of the implant.

The above summary of the present invention is not intended to represent each embodiment, or every aspect, of the present invention. This is the purpose of the figures and the detailed description which follow.

BRIEF DESCRIPTION OF THE DRAWINGS

The foregoing and other advantages of the invention will become apparent upon reading the following detailed description and upon reference to the drawings.

DETAILED DESCRIPTION

The present invention is directed to an implants having discrete nanocrystalline calcium phosphate particles deposited thereon and methods of making the same. An implant in the context of the present invention means a device intended to be placed within a human or mammalian body such as to connect skeletal structures (e.g., a hip implant, a knee implant) or to serve as a fixture for a body part (e.g., a fixture for an artificial tooth). Although the remainder of this application is directed to a dental implant, it is contemplated that the present invention may also be applied to other (e.g., medical) implants.

Figure 1:
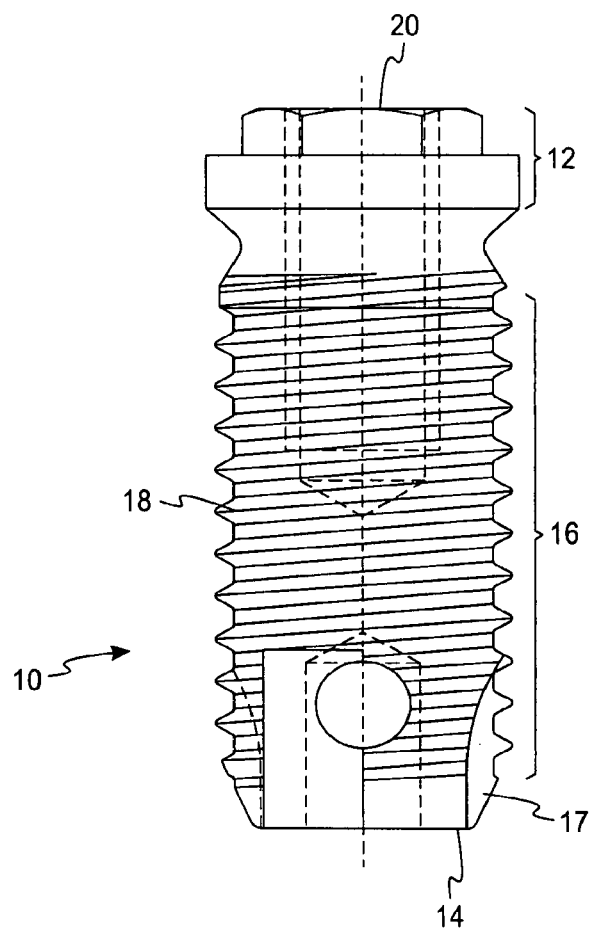
FIG. 1 is a side view of an implant according to one embodiment.

FIG. 1 shows a standard dental implant 10 that includes an head portion 12, a lowermost end 14, and a threaded bottom portion 16. The implant 10 may, for example, be made of titanium, tantalum, cobalt, chromium, stainless steel, or alloys thereof. It is contemplated that other materials such as ceramics or ceramic-titanium combinations may also be used. FIGS. 2a-c, 3a-c, and 4a-b, which are discussed below, describe alternative implant designs that may also be used with the present invention.

In the implant 10 of FIG. 1, the head portion 12 includes a non-rotational feature. In the embodiment shown, the non-rotational feature includes a polygonal boss 20 that may be engageable with a tool that screws the implant 10 into bone tissue. In the illustrated embodiment, the polygonal boss 20 is hexagonal. The polygonal boss 20 may also be used for non-rotationally engaging a correspondingly shaped socket on a restorative or prosthetic component that is attached to the implant 10.

The exterior of the threaded bottom portion 16 facilitates bonding with bone or gingiva. The threaded bottom section 16 includes a thread 18 that makes a plurality of turns around the implant 10. The threaded bottom portion 16 may further include a self-tapping region with incremental cutting edges 17 that allows the implant 10 to be installed without the need for a bone tap. These incremental cutting edges 17 are described in detail in U.S. Pat. No. 5,727,943, entitled "Self-Tapping, Screw-Type Dental Implant," which is incorporated by reference in its entirety.

Figure 2B:
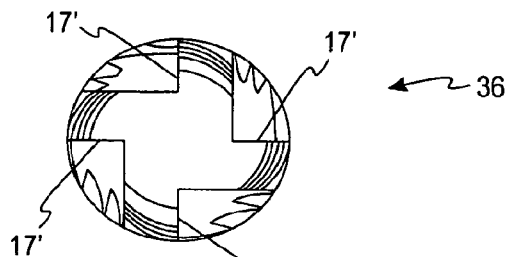
FIGS. 2a, 2b, and 2c, are a side view, an insertion end view, and a gingival end view, respectively, of an implant according to a second embodiment.
Figure 2A:
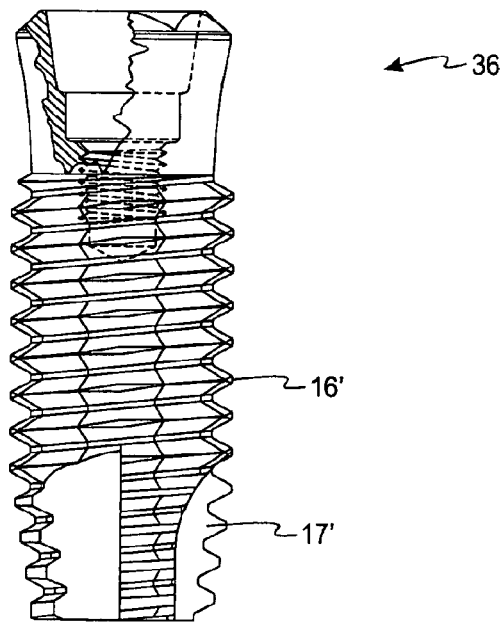
Figure 2C:
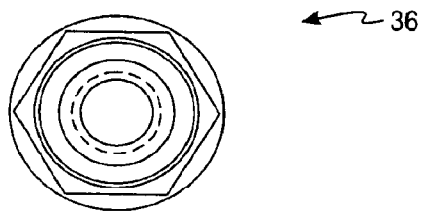

FIGS. 2a-c disclose an implant 36 that differs from the implant 10 of FIG. 1 in the details of the cutting edges 17' and the contours of the threads defining the exterior of the threaded bottom portion 16'. When viewed in the cross-section (see FIG. 1b), the threaded outer surface 16' is non-circular in the region of the threads and/or the troughs between the threads. This type of thread structure is described in detail in U.S. Pat. No. 5,902,109, entitled "Reduced Friction, Screw-Type Dental Implant," which is incorporated by reference in its entirety.

Figure 3B:
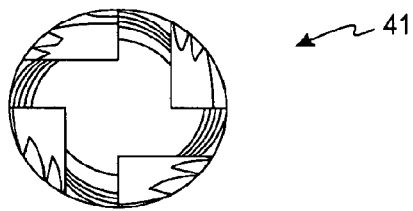
FIGS. 3a, 3b, and 3c, are a side view, an insertion end view, and a gingival end view, respectively, of an implant according to a third embodiment.
Figure 3A:
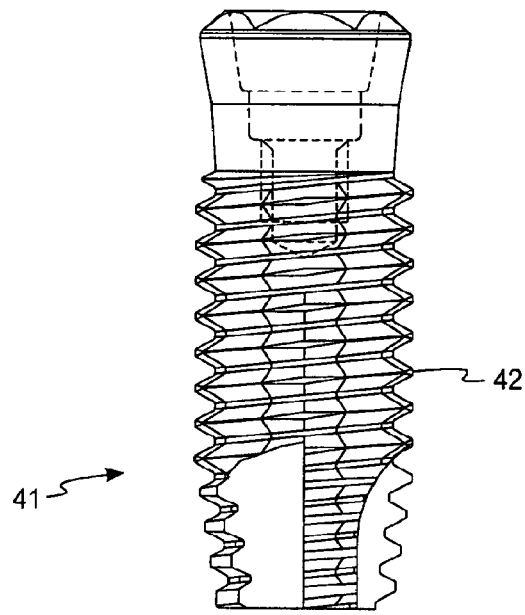
Figure 3C:
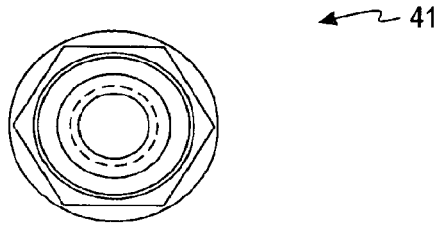

In FIGS. 3a-c, an implant 41 having a wide diameter in the region of the threaded bottom portion 42 is illustrated. The diameter is in the range of from about 4.5 mm to about 6.0 mm with the diameter of 5.0 mm being a fairly common dimension for a wide diameter implant. Such an implant 41 is useful to engage one or both cortical bones to provide enhanced stability, especially during the period of time after installation.

Figure 4B:
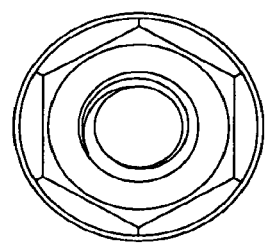
FIGS. 4a and 4b are a side view, an end view, and a cross-sectional view, respectively, of an implant according to a fourth embodiment.
Figure 4A:
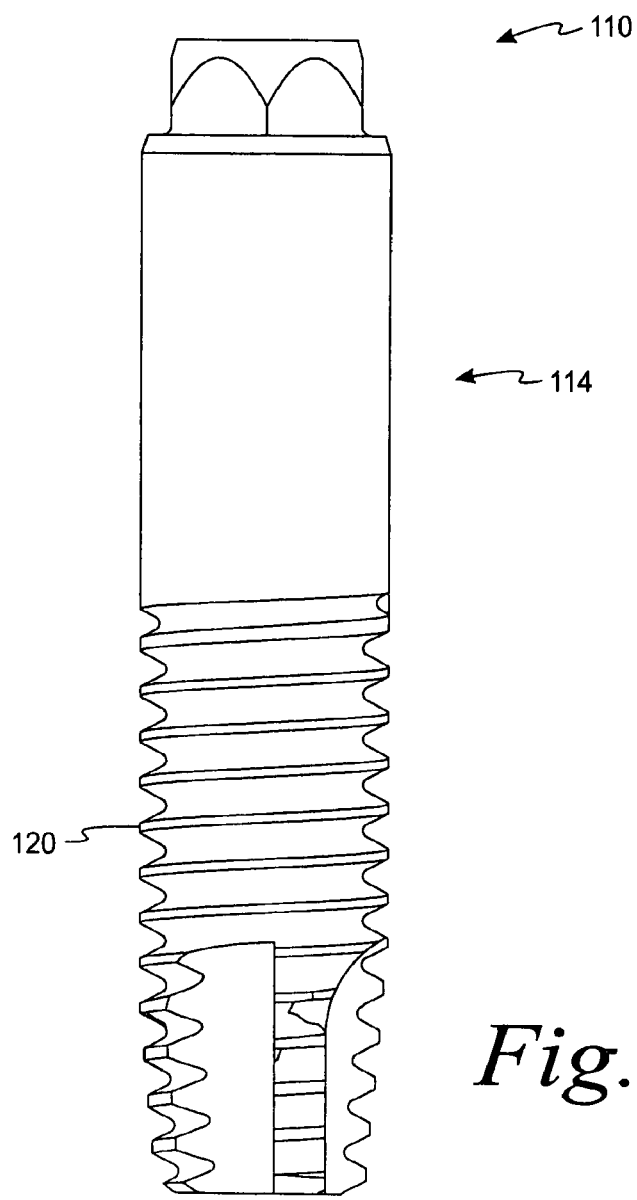

FIGS. 4a-b illustrate an implant 110 according to another embodiment that may be used with the present invention. The implant 110 includes a middle section 114 designed to extend through the gingiva. Preferably, it is a smooth surface that includes a titanium nitride coating so the underlying titanium or titanium alloy is not readily seen through the gingiva. The implant 110 also includes a threaded portion 120 that may include various thread structures and is preferably roughened to increase the osseointegration process. It is contemplated that implants other than those illustrated in FIGS. 1-4 may be used with the present invention.

According to the present invention, a nanoparticle deposition overlies at least a portion (e.g., the threaded bottom portion) of the surface of an implant. In one embodiment, the nanoparticle deposition is a material that promotes osseointegration between the implant and bone material (e.g., human bone material). One suitable material is a calcium phosphate material, such as hydroxyapatite (HA). In one embodiment, the nanoparticle deposition includes HA nanocrystals having dimensions ranging from about 10 nanometers to about 150 nanometers. In another embodiment, the HA nanocrystals have dimensions ranging from about 20 nanometers to about 100 nanometers.

Figure 5:
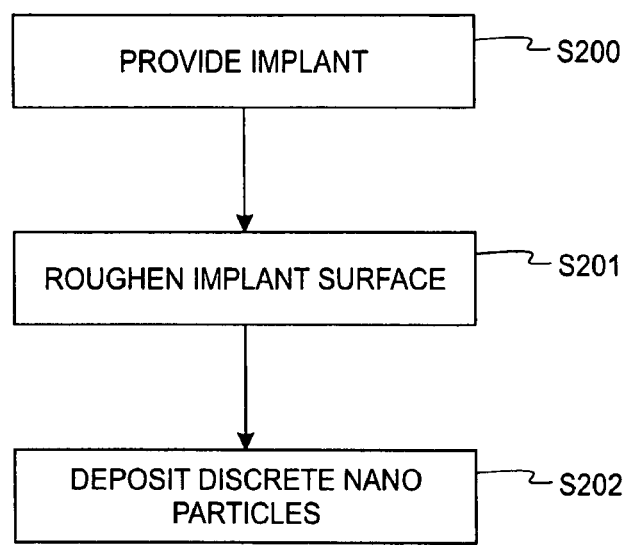
FIG. 5 is a flow diagram detailing a method of forming an implant according to an embodiment of the present invention.
Figure 6:
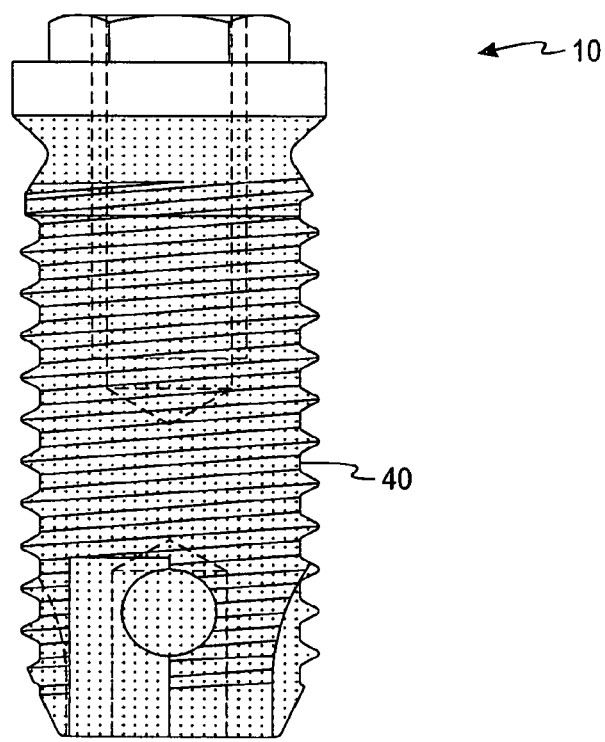
FIG. 6 is a side view of the implant of FIG. 1 with a roughened outer surface.

Turning now to FIG. 5, a general method of depositing nanoparticles of calcium phosphate onto the surface of an implant is set forth according to one embodiment of the present invention. At step s200, an implant is provided. At least a portion of the implant surface is roughened at step s201. As an example, FIG. 6 shows the implant 10 of FIG. 1 having a roughened surface 130. Discrete nanoparticles comprising a material having a property that promotes osseointegration are then deposited onto the roughened surface of the implant at step s202.

Figure 7A:
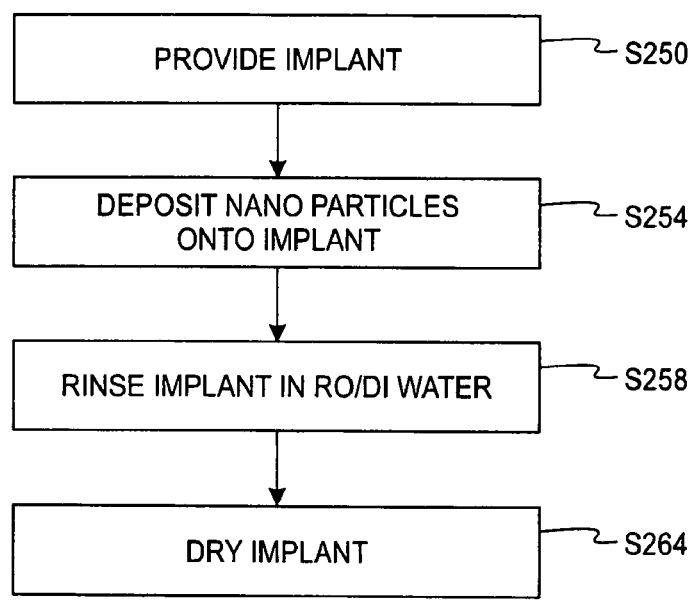
FIG. 7a is a flow diagram detailing a method of forming an implant according to another embodiment of the present invention.

Referring now to FIG. 7a, another general method of forming an implant according to another embodiment of the present invention is illustrated. An implant comprised of titanium, a titanium alloy (e.g., titanium 6AL-4V ELI alloy), stainless steel, ceramic, or the like is provided at step s250. At step s254, discrete nanoparticles comprising a material having a property that promotes osseointegration (e.g., HA nanocrystals) are then deposited onto the roughened surface of the implant. The implant may then be rinsed in reverse osmosis/deionized (RO/DI) water to remove residual solvents and HA at step s258. The implant is then dried at step s264.

Figure 7B:
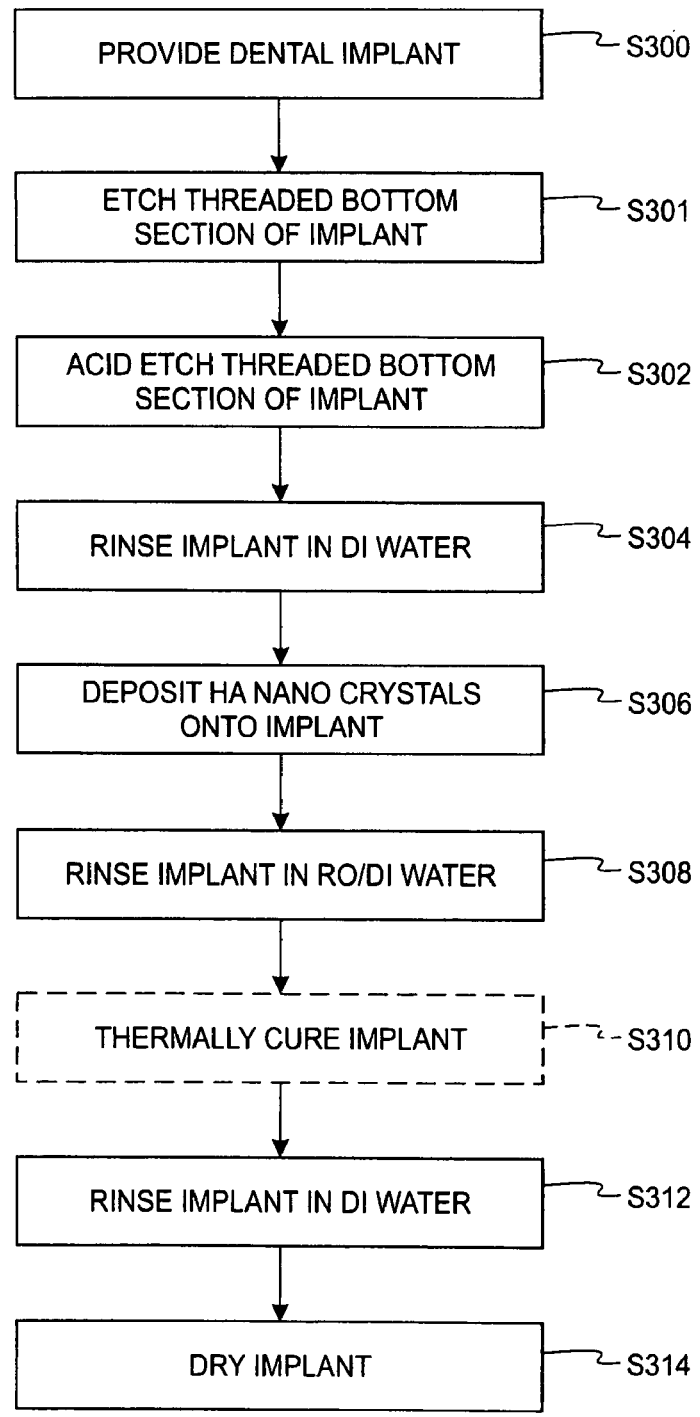
FIG. 7b is a flow diagram detailing a method of forming an implant according to yet another embodiment of the present invention.

Referring to FIG. 7b, a more detailed method of depositing HA nanocrystals onto the surface of a dental implant is illustrated according to another embodiment of the present invention. A threaded dental implant comprised of titanium, a titanium alloy (e.g., titanium 6AL-4V ELI alloy), stainless steel, or the like is provided at step s300. The surface of the dental implant is generally clean and dry. A threaded bottom portion of the implant is etched to remove a native oxide layer from the implant surface at step s301. The native oxide layer may be removed by a first acid solution, which may include aqueous hydrofluoric acid. The threaded bottom portion is then acid etched to form a roughened surface at step s302. The acid etching step may include a mixture of sulfuric and hydrochloric acids. The roughened surface forms a substantially uniform array of microscale irregularities for enhancing the integration of the implant with bone or other biological interfaces. "Microscale," as used herein, should be understood to describe an article or feature generally measured in microns such as, for example, 1 micron to 100 microns. The irregularities may include micro scale cone-shaped elements and generally have peak-to-valley heights not greater than about 20 microns and are preferably about 1 micron to about 10 microns. This type of roughening method utilized on commercially pure (CP) titanium is described in detail in U.S. Pat. No. 5,876,453 entitled "Implant Surface Preparation," which is incorporated by reference in its entirety. An additional roughening method utilized on Titanium 6AL-4V ELI alloy is described in detail in U.S. Pat. App. Pub. No. 2004/0265780 entitled "Surface Treatment Process for Implants Made of Titanium Alloy," which is also incorporated by reference in its entirety. It is contemplated that other surface roughening techniques including, but not limited to, grit blasting and titanium plasma spray may be used. After these acid-etching steps, the implant may then be rinsed in hot deionized water (e.g., 70° C. to 100° C.) to remove any acid residuals and to potentially enhance titanium hydroxide groups on the surface at step s304.

The HA nanocrystals are then deposited onto the roughened surface of the implant at step s306. The HA nanocrystals may be introduced onto the roughened surface of the implant in the form of a colloid. A representative amount of HA in the colloid is typically in the range of about 0.01 weight percent to about 1 weight percent (e.g., 0.10 weight percent). To form the colloid, HA nanocrystals may be combined in solution with a 2-methoxyethanol solvent and ultrasonically dispersed and deagglomerated. The pH of the colloidal solution may be adjusted with sodium hydroxide, ammonium hydroxide, or the like on the order of about 7 to about 13. As such, the colloidal solution may include HA nanocrystals, 2-methoxyethanol, and a pH adjuster (e.g., ammonium hydroxide, and/or sodium hydroxide).

In preparing a solution of HA nanocrystals, raw HA nanocrystal material may be refined to achieve a stock solution with limited agglomeration of crystals. According to one method, BABI-HAP-N20-E HA material, manufactured by Berkley Advanced Biomaterials (Berkley, Calif.), is dried to form a cake. The cake is then mechanically crushed into a fine powder and subsequently combined with a 2-methoxyethanol solution. The solution is then ultrasonically dispersed to de-agglomerate the HA nanocrystals. The solution is then allowed to settle and is decanted. A top portion of the settled solution is used as a stock solution for manufacturing a deposition solution. The stock solution is tested to confirm particle size distribution and HA concentration. An appropriate particle size distribution (volume) as indicated by the Nanotrac 150 (Microtrac, Inc., North Largo, Fla.) has a D10 (tenth percentile distribution) of less than 150 nanometers, a D50 (fiftieth percentile distribution) of less than 300 nanometers, and a D90 (ninetieth percentile distribution)) of less than 900 nanometers.

The deposition solution is prepared by combining the stock solution of appropriately sized HA nanocrystals in 2-methoxyethanol with additional 2-methoxyethanol to achieve a desired concentration. One such concentration ranges from about 0.08 weight percent to about 0.12 weight percent HA in 2-methoxyethanol. It is contemplated that the concentration of HA may be lower than 0.08 weight percent or higher than 0.12 weight percent, provided that other variables (e.g., immersion time and pH) are modified accordingly.

The deposition solution may be pH adjusted with, for example, ammonium hydroxide. More basic solutions generally accelerate the deposition process and allow larger particles to be deposited on the implant surface. Suitable concentrations may range from between about 0.05 weight percent to about 0.1 weight percent ammonium hydroxide. A 25% by weight combination of the pH adjusted deposition solution with deionized water generally has a pH of about 9 to about 11.

The HA nanocrystals are then deposited on the surface of the implant by, for example, dipping the implant into the colloidal solution. The solution may be mixed initially but is generally stagnant during deposition. The implant may, for example, be immersed in the colloidal solution for several hours (e.g., 2 hours to 4 hours). The deposition may be performed at generally ambient temperatures or at temperatures higher or lower than ambient temperature. The HA nanocrystals bond directly to the titanium hydroxide and/or titanium oxide.

Immersion time and HA concentration are among several factors that affect the rate and amount of deposition of HA nanocrystals onto the implant surface. Immersing the implant in a solution having a concentration of about 0.1 weight percent HA and a pH of approximately 10 for about 60 minutes, for example, typically results in deposition covering about 40% to about 60% of the implant surface. Longer immersion times generally provide greater coverage and may form a layer or coating on the implant surface. Conversely, shorter immersion times generally decrease the amount of material deposited on the implant surface. Solutions having lower concentrations of HA nanocrystals generally require longer immersion times, whereas solutions having higher concentrations of HA nanocrystals generally require shorter immersion times.

Another factor affecting the rate and amount of deposition of HA nanocrystals onto the implant surface is the pH of the deposition solution. The pH of the solution also affects, to some degree, the size of the HA nanocrystals that are deposited on the implant. At an acidic pH (i.e., less than 7), the deposition rate is generally slow, and the average size of the particles deposited onto the implant surface generally decreases. At a neutral pH (approximately 7), the deposition occurs relatively slowly. For example, if a deposition solution having an HA concentration of about 0.1 weight percent is used, the implant must be immersed for about 2 hours to about 4 hours to achieve about 40% to about 60% coverage. Additionally, the particles deposited on the surface are generally smaller (about 20 nanometers) and more uniform. At an elevated pH (i.e., greater than 9), the size of the HA nanocrystals deposited is generally greater, ranging from about 20 nanometers to about 150 nanometers. The process time for a solution having an HA concentration of about 0.1 weight percent and a pH greater than about 9 is also generally shorter, with an immersion time of 60 minutes resulting in deposition coverage of about 40% to about 60%.

The implant may then be rinsed in reverse osmosis/deionized (RO/DI) water to remove residual solvent and HA at step s308. The implant is then dried (e.g., oven dried). At optional step s310, the implant may then be thermally cured to sinter the HA at a temperature ranging from approximately 80° C. to approximately 500° C. (e.g., about 100° C.).

Additional acts may then be performed to correct potential aesthetic discoloration of the implants that may occur during the method of depositing the HA nanocrystals on the implant. For example, at step s312, the implant is rinsed in deionized water at a temperature ranging from approximately 40° C. to approximately 80° C. to remove any water spotting that may have formed on the implant. The implant may then be dried. The implant may, for example, be oven dried at a temperature ranging from approximately 80° C. to approximately 500° C. at step s314.

The implant surface may be characterized utilizing Field Emission Scanning Electron microscopy (FESEM). Depending upon the resolution of the instrument, the deposition of the nanoparticles may typically be witnessed at magnifications of over 10 kX (e.g., 30 kX). The amount of discrete nanocrystalline deposition coverage may be analyzed by conducting contrast phase analysis on FESEM images using computer software. The adhesion of nanocrystals to the surface of an implant may be verified through functional testing or novel techniques such as testing adhesion strength (e.g., shear strength) using atomic force microscopy and a nanometer length scale silica nitride (SiN) calibrated beam with a diamond coated probe or tip.

According to another method of the present invention, discrete nanoparticles (e.g., HA nanocrystals) are deposited onto an implant surface without first roughening the surface of the implant. In this embodiment, the implant is machined, and its final surface configuration is generally smooth as compared to the acid-etching steps previously described.

The colloidal solutions referred to in Examples 1-10 below were prepared using the processes previously set forth above. After the HA nanocystals were deposited on the implant surface in Examples 1-10, the implants were oven dried at a temperature of approximately 100° C.

EXAMPLE 1

Figure 8A:
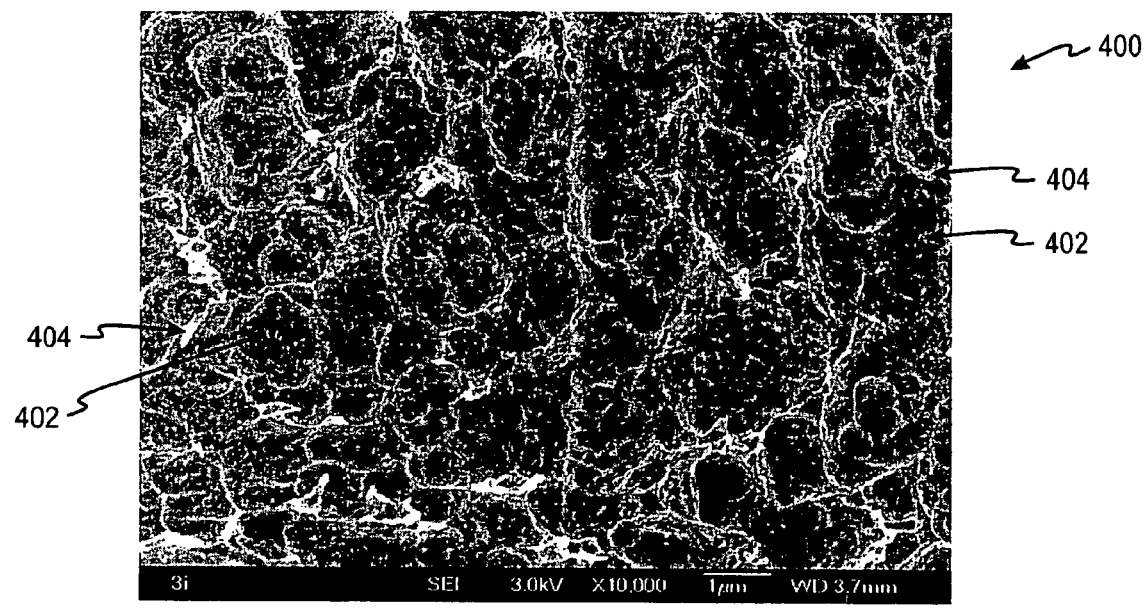
FIG. 8a is a field emission scanning electron microscope (FESEM) image showing hydroxyapatite nanoparticles at 10 kX.
Figure 8B:
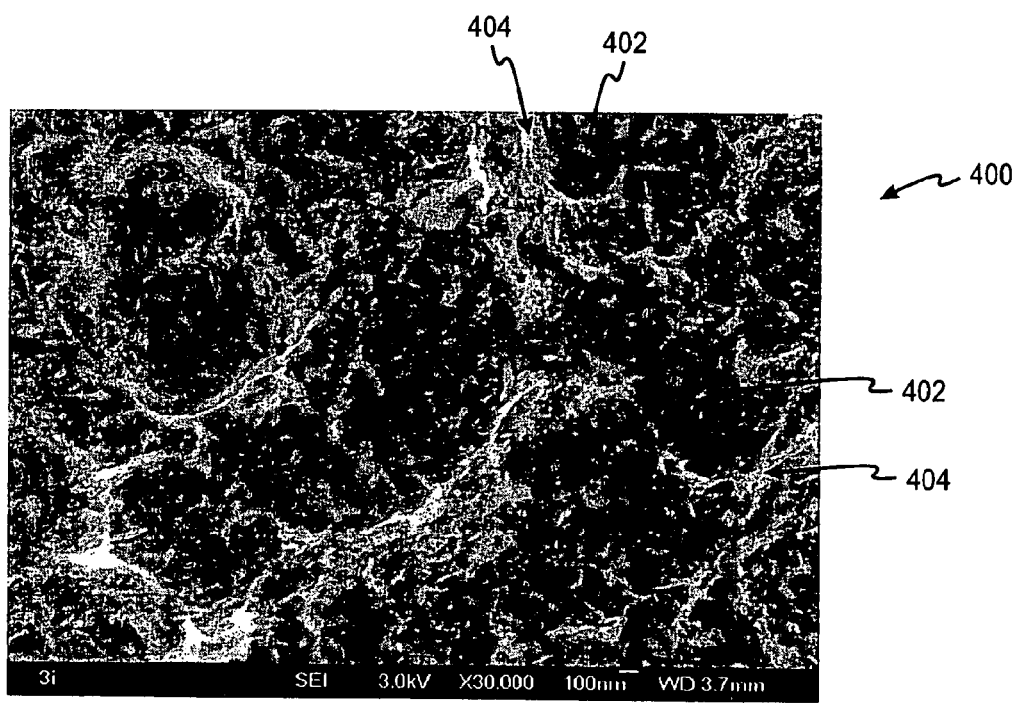
FIG. 8b is an FESEM image showing hydroxyapatite nanoparticles at 30 kX.

FIGS. 8a, 8b are scanning electron microscope images showing HA nanocrystals 402 after being deposited on the surface of a CP titanium implant 400. The image of FIG. 8a was taken at 10 kX utilizing an FESEM. The image of FIG. 8b was taken at 30 kX utilizing an FESEM.

The surface of the implant 400 shown in FIGS. 8a, 8b was roughened using a citric acid etching process, described in U.S. patent application Ser. No. 11/361,286, which has been incorporated by reference herein, to produce an Osseotite® surface. The roughening process resulted in irregularities 404 having peak-to-valley heights of no more than 10 microns. The HA nanocrystals 402 were deposited on the surface of the implant 400 using a colloidal solution. The colloidal solution included about 0.07 weight percent of HA in a 2-methoxyethanol solvent. The implant 400 was immersed in the colloidal solution for approximately 4 hours. The resulting deposition of HA nanocrystals 402 on the implant 400 are shown in FIGS. 8a, 8b.

EXAMPLE 2

Figure 9A:
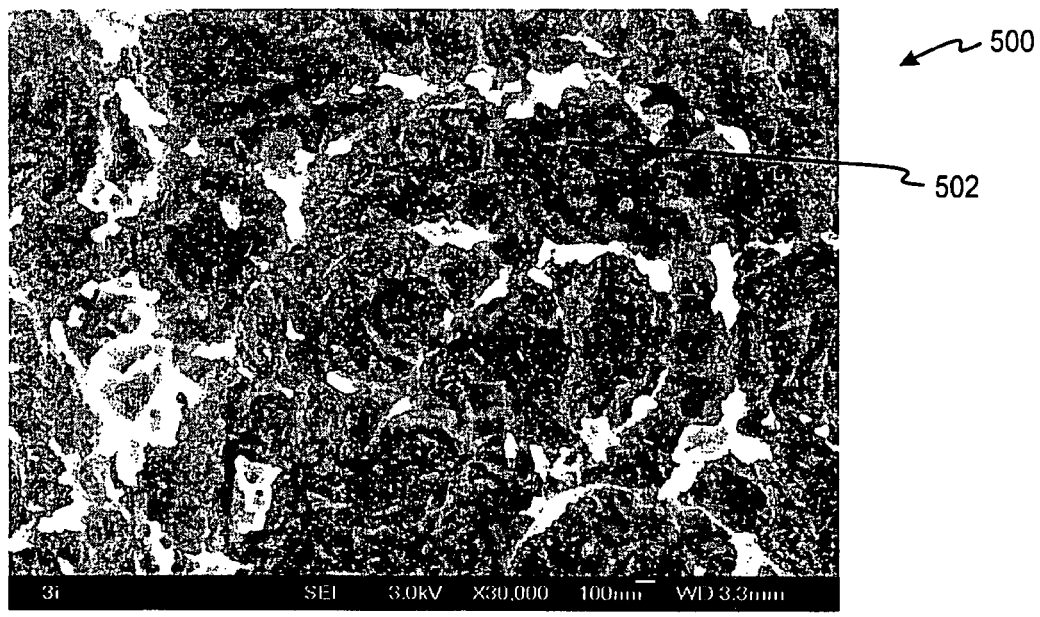
FIGS. 9a-13c are FESEM images showing hydroxyapatite nanoparticles at 30 kX deposited onto an implant surface using various methods of the present invention.

FIG. 9a is a scanning electron microscope image showing HA nanocrystals 502 after being deposited on the surface of an implant 500. The image of FIG. 9a was taken at 30 kX utilizing an FESEM.

The implant 500 used in FIG. 9a was comprised of titanium 6AL-4V ELI alloy. The surface of the implant 500 shown in FIG. 9a was roughened using the dual acid-etched process described in U.S. Pat. App. Pub. No. 2004/0265780, which has been incorporated by reference herein. The HA nanocrystals 502 were deposited on the surface of the implant 500 using a colloidal solution described above including about 0.10 weight percent of HA in a 2-methoxyethanol solvent. The implant 500 was immersed in the colloidal solution for approximately 150 minutes at ambient temperature. The resulting deposition of HA nanocrystals 502 on the implant 500 is shown in FIG. 9a.

EXAMPLE 3

Figure 9B:

FIG. 9b is a scanning electron microscope image showing HA nanocrystals 552 after being deposited on the surface of a titanium 6AL-4V ELI alloy implant 550. The image of FIG. 9b was taken at 30 kX utilizing an FESEM.

The procedure used for depositing the HA nanocrystals 552 on the surface of the implant 550 was generally similar to the procedure used in Example 2. However, unlike the procedure of Example 2, the pH of the colloidal solution of Example 3 was adjusted with ammonium hydroxide to 0.10 weight percent ammonium hydroxide. The pH of the adjusted solution was between 9 and 10 when measured at about 25 weight percent in deionized $H_2O$. The implant 550 was immersed in the colloidal solution for approximately 60 minutes at ambient temperature. The resulting deposition of HA nanocrystals 552 on the implant 550 is shown in FIG. 9b.

As shown in FIG. 9b, deposition of HA nanocrystals 552 on the surface of the implant 550 is comparable to that of the implant 500 of FIG. 9a. However, the immersion time of the implant 550 was considerably shorter. Thus, adjusting the pH to form a more basic solution was shown to shorten the process time required for deposition of the HA nanocrystals 552 on the surface of the implant.

EXAMPLE 4

Figure 9C:

FIG. 9c is a scanning electron microscope image showing HA nanocrystals 602 after being deposited on the surface of a titanium 6AL-4V ELI alloy implant 600. The image of FIG. 9c was taken at 30 kX utilizing an FESEM.

The procedure used for depositing the HA nanocrystals 602 on the surface of the implant 600 was similar to the procedure used in Example 3. However, unlike the implant 550 of Example 3, the surface of the implant 600 shown in FIG. 9c was not roughened. Rather, the surface of the implant 600 was machined, and its final surface configuration prior to depositing the HA nanocrystals 602 was generally smooth.

As shown in FIG. 9c, the deposition of HA nanocrystals 602 on the surface of the implant 600 is comparable to that of the implants 500, 550 of FIGS. 9a and 9b respectively. Thus, adequate deposition of HA nanocrystals on an implant surface may occur without roughening the implant surface prior to deposition.

EXAMPLE 5

Figure 9D:
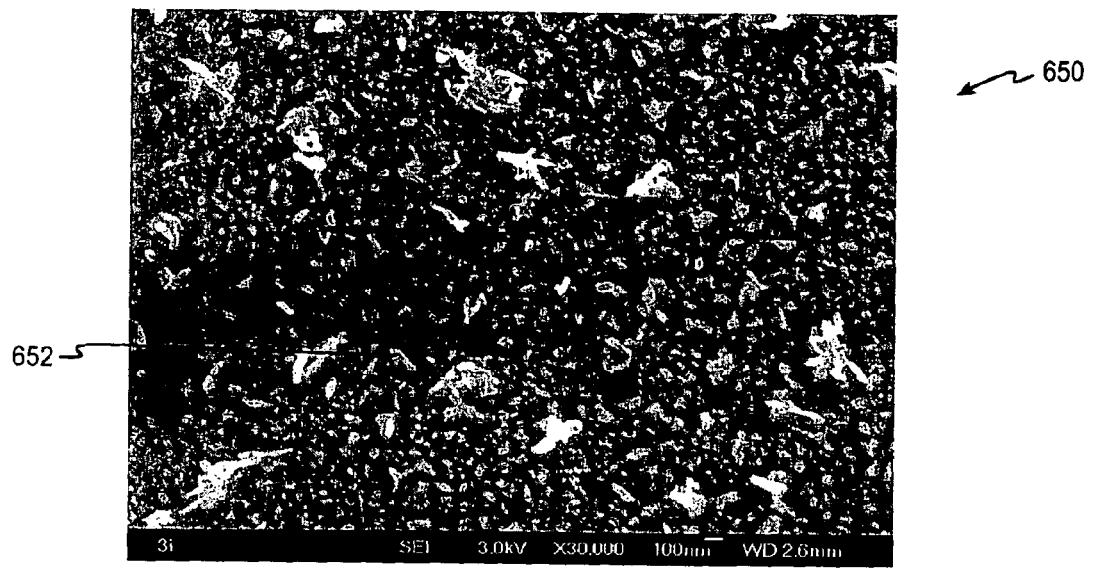

FIG. 9d is a scanning electron microscope image showing HA nanocrystals 652 after being deposited on the surface of an implant 650. The image of FIG. 9d was taken at 30 kX utilizing an FESEM.

The procedure used for depositing the HA nanocrystals 652 on the surface of the implant 650 was similar to the procedure used in Example 3. However, the implant 650 used in FIG. 9d was comprised of 316 stainless steel such that it could be used on, for example, a cortical screw. The surface of the substrate was not roughened prior to deposition. The implant 650 was immersed in the colloidal solution for approximately 120 minutes at ambient temperature. The resulting deposition of HA nanocrystals 652 on the implant 650 is shown in FIG. 9d.

As shown in FIG. 9d, the amount of HA nanocrystals 652 deposited on the surface of the implant 650 is comparable to that of FIGS. 9a-c. Thus, adequate deposition of HA nanocrystals on an implant surface may occur on implants comprising metals other than titanium and titanium alloys (e.g., stainless steel).

EXAMPLE 6

Figure 10:
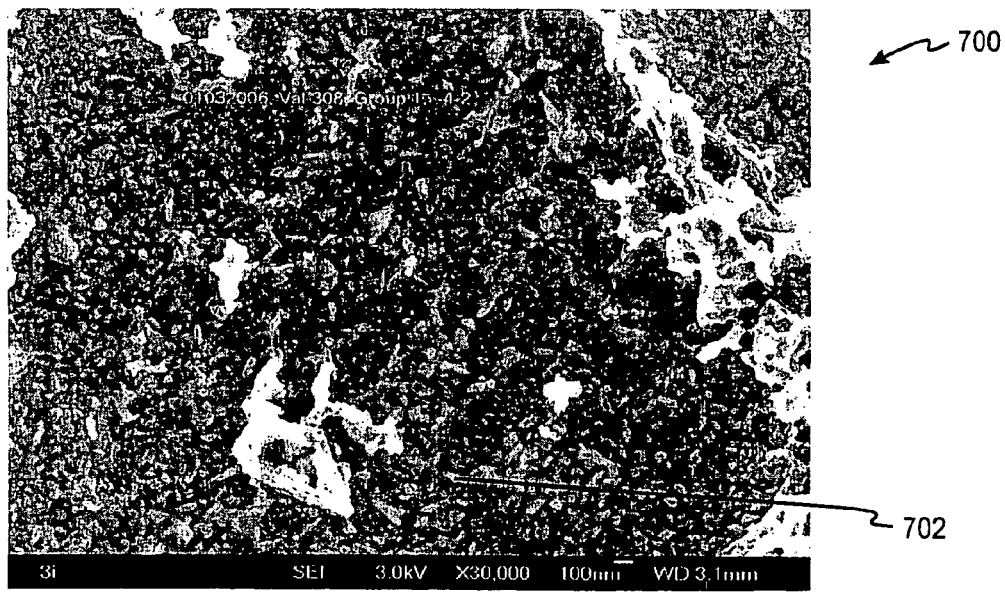

FIG. 10 is a scanning electron microscope image showing HA nanocrystals 702 after being deposited on the surface of an implant 700. The image of FIG. 10 was taken at 30 kX utilizing an FESEM.

The implant 700 used in FIG. 10 was comprised of titanium 6AL-4V ELI alloy. The surface of the implant 700 shown in FIG. 10 was roughened using the dual acid-etched process described in U.S. Pat. App. Pub. No. 2004/0265780, which has been incorporated by reference herein. The HA nanocrystals 702 were deposited on the surface of the implant 700 using a colloidal solution including about 0.80 weight percent of HA in a 2-methoxyethanol solvent. The pH of the colloidal solution was adjusted with ammonium hydroxide to 0.01 weight percent ammonium hydroxide. The pH of the adjusted solution was between 8 and 9 when measured at about 25 weight percent in deionized $H_2O$. The implant 700 was immersed in the colloidal solution for approximately 55 minutes at a temperature of about 18° C. The resulting deposition of HA nanocrystals 702 on the implant 700 is shown in FIG. 10.

The procedure of Example 6 utilized a lower concentration of HA nanocrystals (i.e., 0.08 weight percent) and a relatively low concentration of ammonium hydroxide (i.e., 0.01 weight percent). The deposition of HA nanocrystals 702 on the surface of the implant 700, however, is comparable to that of FIGS. 9a-d.

EXAMPLE 7

Figure 11:
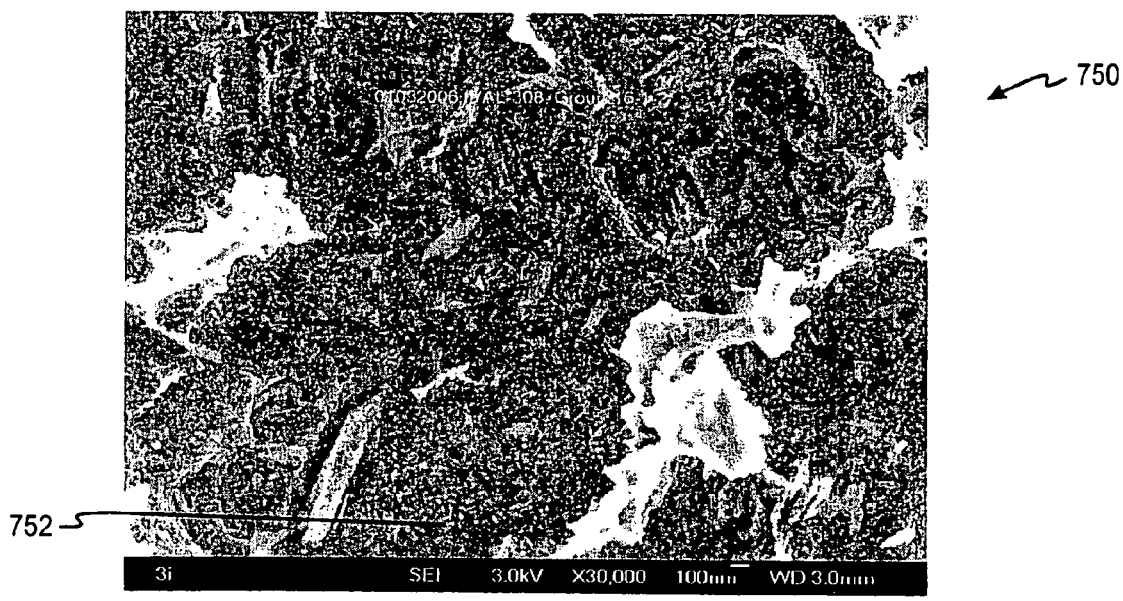

FIG. 11 is a scanning electron microscope image showing HA nanocrystals 752 after being deposited on the surface of an implant 750. The image of FIG. 11 was taken at 30 kX utilizing an FESEM.

The implant 750 used in FIG. 11 was comprised of titanium 6AL-4V ELI alloy. The surface of the implant 750 shown in FIG. 11 was roughened using the dual acid-etched process described in U.S. Pat. App. Pub. No. 2004/0265780, which has been incorporated by reference herein. The HA nanocrystals 752 were deposited on the surface of the implant 750 using a colloidal solution including about 0.12 weight percent of HA in a 2-methoxyethanol solvent. The pH of the colloidal solution was adjusted with ammonium hydroxide to 0.30 weight percent ammonium hydroxide. The pH of the adjusted solution was between 10 and 11 when measured at about 25 weight percent in deionized $H_2O$. The implant 550 was immersed in the colloidal solution for approximately 70 minutes at a temperature of about 30° C. The resulting deposition of HA nanocrystals 752 on the implant 750 is shown in FIG. 11.

The procedure of Example 7 utilized a higher concentration of HA nanocrystals (i.e., 0.12 weight percent) than that of Example 6 (i.e., 0.08 weight percent). The procedure of Example 7 also substantially increased the concentration of ammonium hydroxide (i.e., 0.30 weight percent) as compared to the procedure of Example 6. The deposition of HA nanocrystals 752 on the surface of the implant 750, however, is comparable to those of the examples above.

EXAMPLE 8

Figure 12A:
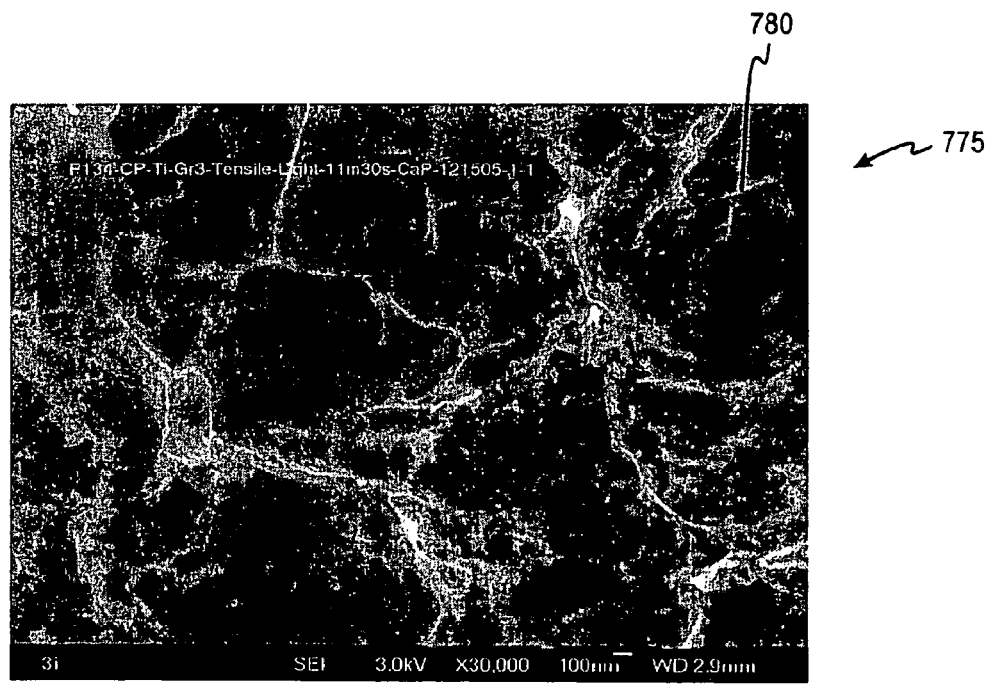

FIG. 12a is a scanning electron microscope image showing HA nanocrystals 780 after being deposited on the surface of an implant 775. The image of FIG. 12a was taken at 30 kX utilizing an FESEM.

The implant 775 used in FIG. 12a was comprised of CP titanium. The surface of the implant 775 shown in FIG. 12a was roughened using the dual acid-etched process described in U.S. Pat. No. 5,876,453, which has been incorporated by reference herein. The HA nanocrystals 780 were deposited on the surface of the implant 775 using a colloidal solution including about 0.1 weight percent of HA in a 2-methoxyethanol solvent. The pH of the colloidal solution was adjusted with ammonium hydroxide to 0.05 weight percent ammonium hydroxide. The pH of the adjusted solution was between 9 and 10 when measured at about 25 weight percent in deionized $H_2O$. The implant 775 was immersed in the colloidal solution for approximately 11.5 minutes at ambient temperature. The immersion time, 11.5 minutes, is relatively low compared to that of the previous examples. Accordingly, the amount of HA nanocrystals 780 deposited on the surface of the implant 775 is generally less than those of the previous examples.

EXAMPLE 9

Figure 12B:
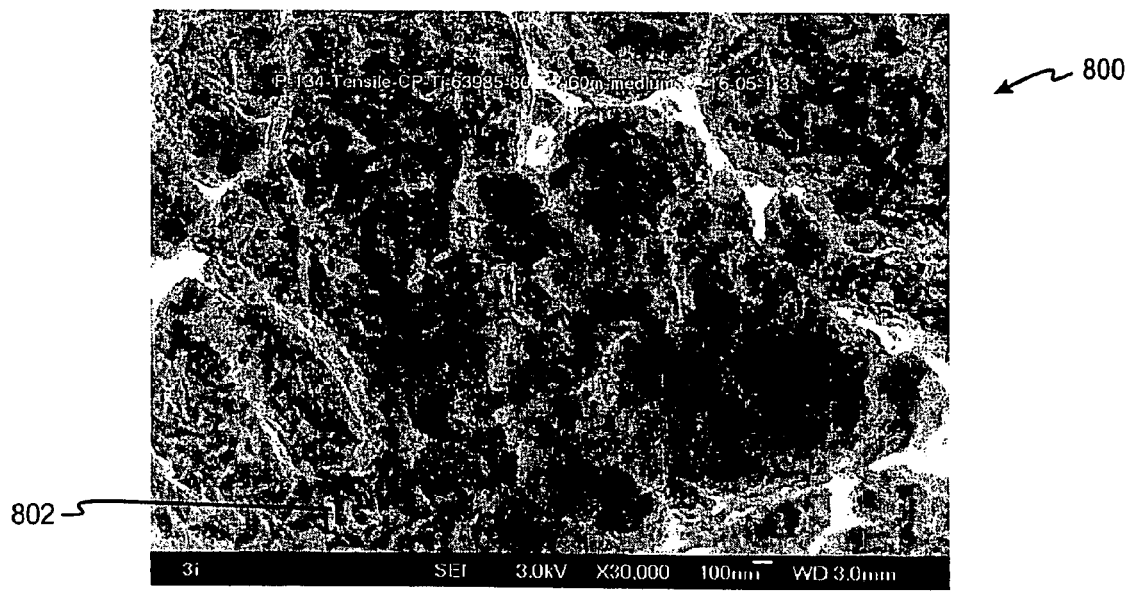

FIG. 12b is a scanning electron microscope image showing HA nanocrystals 802 after being deposited on the surface of a CP titanium implant 800. The image of FIG. 12b was taken at 30 kX utilizing an FESEM.

The procedure used for depositing the HA nanocrystals 802 on the surface of the implant 800 was similar to the procedure used in Example 8. However, the immersion time used in FIG. 12b was approximately 60 minutes. Thus, the immersion time is higher than that of Example 8. Accordingly, the amount of HA nanocrystals 802 deposited on the surface of the implant 800 is generally greater than that of Example 8.

EXAMPLE 10

Figure 12C:
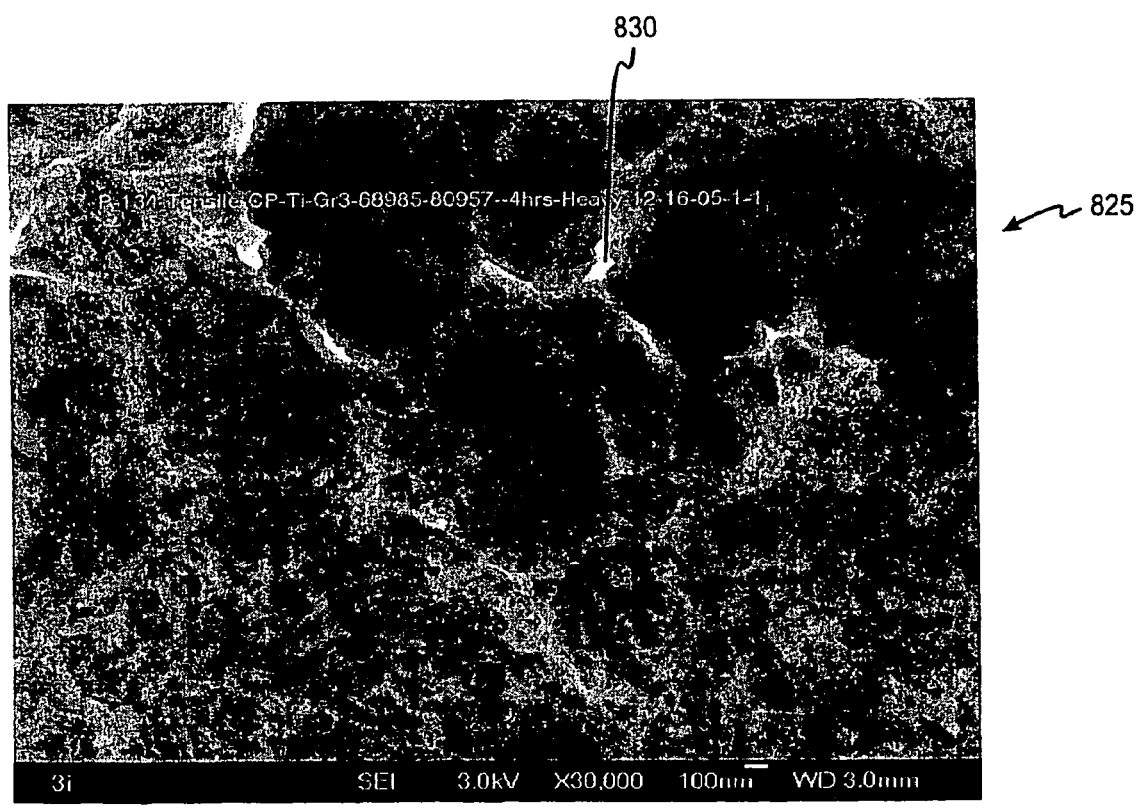

FIG. 12c is a scanning electron microscope image showing HA nanocrystals 830 after being deposited on the surface of a CP titanium implant 825. The image of FIG. 12c was taken at 30 kX utilizing an FESEM.

The procedure used for depositing the HA nanocrystals 830 on the surface of the implant 825 was similar to the procedure used in Examples 8 and 9. However, the immersion time used in FIG. 12c was approximately 240 minutes. Thus, the immersion time is considerably higher than those of Examples 8 and 9. Accordingly, the amount of HA nanocrystals 830 deposited on the surface of the implant 825 is generally greater than those of Examples 8 and 9.

EXAMPLE 11

Figure 13A:
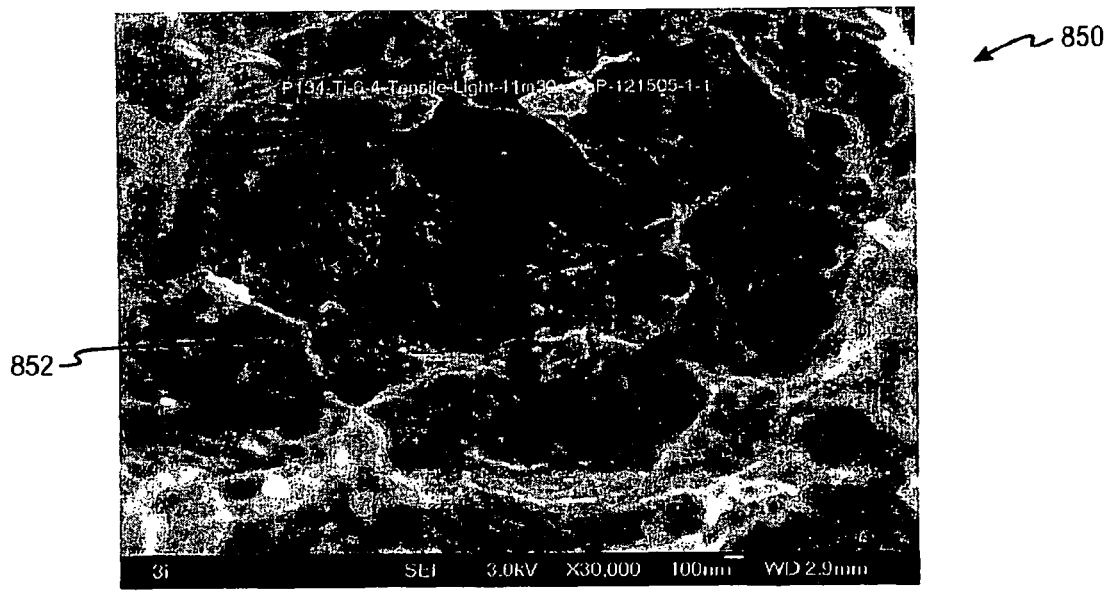

FIG. 13a is a scanning electron microscope image showing HA nanocrystals 852 after being deposited on the surface of an implant 850. The image of FIG. 13a was taken at 30 kX utilizing an FESEM.

The implant 850 used in FIG. 13a was comprised of titanium 6AL-4V ELI. The surface of the implant 850 shown in FIG. 13a was roughened using the dual acid-etched process described in U.S. Pat. App. Pub. No. 2004/0265780, which has been incorporated by reference herein. The HA nanocrystals 852 were deposited on the surface of the implant 850 using a colloidal solution including about 0.10 weight percent of HA in a 2-methoxyethanol solvent. The pH of the colloidal solution was adjusted with ammonium hydroxide to 0.05 weight percent ammonium hydroxide. The implant 850 was immersed in the colloidal solution for approximately 11.5 minutes at ambient temperature.

The resulting deposition of HA nanocrystals 852 on the implant 850 is shown in FIG. 13a. The immersion time, 11.5 minutes, is relatively low compared to that of the previous examples. Accordingly, the amount of HA nanocrystals 852 deposited on the surface of the implant 850 is generally less than those of the previous examples.

EXAMPLE 12

Figure 13B:
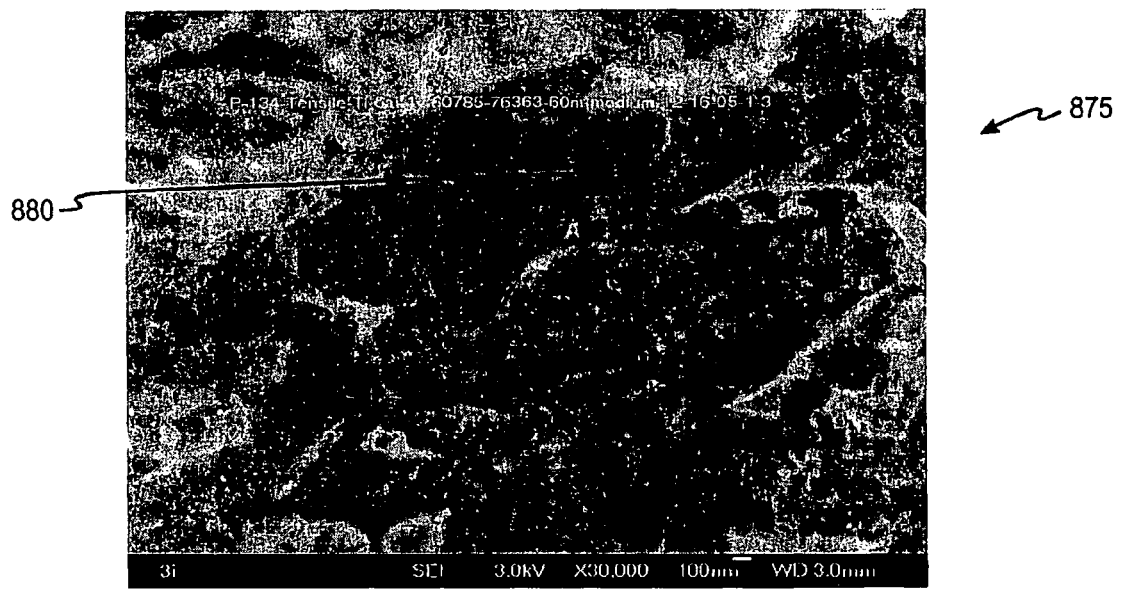

FIG. 13b is a scanning electron microscope image showing HA nanocrystals 880 after being deposited on the surface of a titanium 6AL-4V ELI alloy implant 875. The image of FIG. 13b was taken at 30 kX utilizing an FESEM.

The procedure used for depositing the HA nanocrystals 880 on the surface of the implant 875 was similar to the procedure used in Example 11. However, the immersion time used in FIG. 13b was approximately 60 minutes. Thus, the immersion time is higher than that of Example 11. Accordingly, the amount of HA nanocrystals 880 deposited on the surface of the implant 875 is generally greater than that of Example 11.

EXAMPLE 13

Figure 13C:
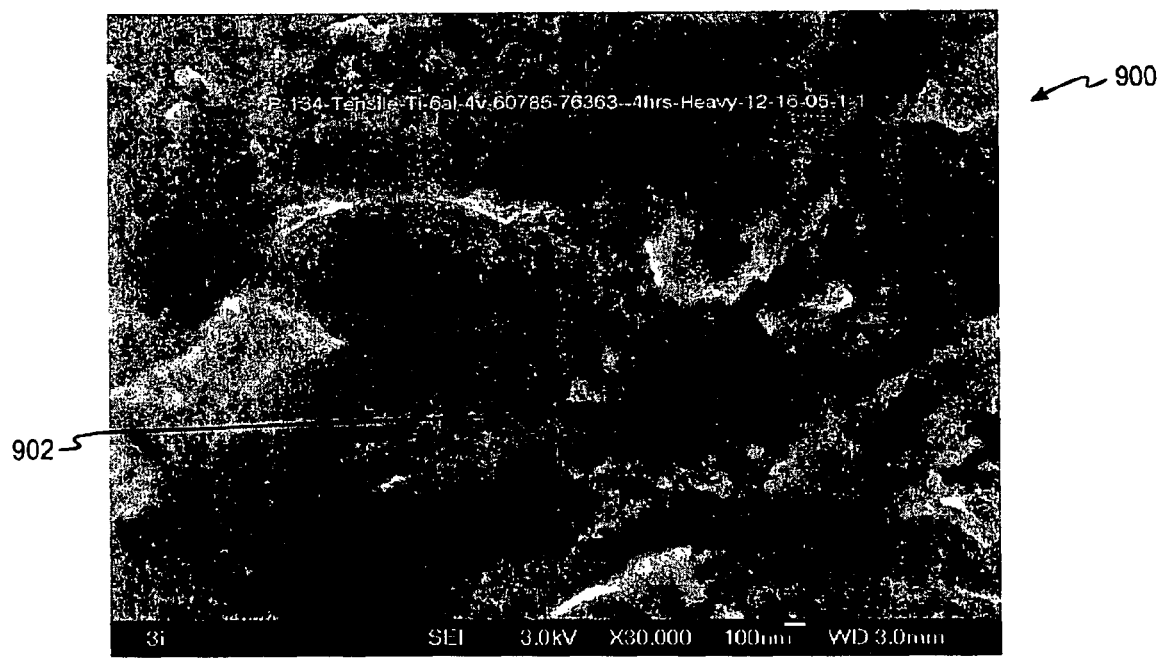

FIG. 13c is a scanning electron microscope image showing HA nanocrystals 902 after being deposited on the surface of a titanium 6AL-4V ELI alloy implant 900. The image of FIG. 13c was taken at 30 kX utilizing an FESEM.

The procedure used for depositing the HA nanocrystals 902 on the surface of the implant 900 was similar to the procedure used in Example 9. However, the immersion time used in FIG. 13c was approximately 240 minutes. Thus, the immersion time is considerably higher than that of Examples 11 and 12. Accordingly, the amount of HA nanocrystals 902 deposited on the surface of the implant 900 is generally greater than those of Examples 11 and 12.

Laboratory Testing on Animals

An animal study was conducted to test the performance of several implants having HA nanocrystals deposited thereon. The study utilized a bone-to-implant tensile strength test comparing the results of two control groups and six test groups. The control groups included Osseotite® etched titanium alloy (6AL-4V ELI) implants and commercially pure (CP) titanium implants. Three of the test groups included Osseotite® etched CP titanium implants with HA nanocrystals deposited thereon. The remaining three test groups included Osseotite® etched titanium alloy (6AL-4V ELI) implants with HA nanocrystals deposited thereon. The test groups differed in the level of coverage (light, medium, and heavy) of the HA nanocrystals on the respective implants. Twelve implants were tested for each of the six test groups and two control groups.

CP titanium implants like the implants 775, 800, 825 shown in FIGS. 12a-c and described in Examples 8, 9, and 10 above were also among the implants tested during the study. Implants made pursuant to Example 8 (FIG. 12a) were among the group of Osseotite® CP titanium implants having light coverage. Implants made pursuant to Example 9 (FIG. 12b) were among the group of Osseotite® CP titanium implants having medium coverage. Implants made pursuant to Example 10 (FIG. 12c) were among the group of Osseotite® CP titanium implants having heavy coverage.

Titanium alloy implants like the implants 850, 875, 900 shown in FIGS. 13a-c and described in Examples 11, 12, and 13 above were among the implants tested during the study. Implants made pursuant to Example 11 (FIG. 13a) were among the group of Osseotite® titanium 6AL-4V ELI implants having light coverage. Implants made pursuant to Example 12 (FIG. 13b) were among the group of Osseotite® titanium 6AL-4V ELI implants having medium coverage. Implants made pursuant to Example 13 (FIG. 13c) was among the group of Osseotite® titanium 6AL-4V ELI implants having heavy coverage.

The tensile strength test study was conducted utilizing rats as the test subjects. The implants were surgically implanted into both femurs of the test subjects in a bi-cortical manner. The implantation site was then closed and allowed to heal for nine days, after which the test subjects were sacrificed. The subject femurs were then removed, and the bone/implant cross sections were prepped for the tensile strength testing. Wires were then inserted through the medullary cavity on both sides of the implant. The implants were subsequently fixed on an Instron® Universal Testing System, manufactured by Instron Corporation® (Burlington, Ontario). The wire was pulled vertically with increasing force until the bone broke away from the implant. The maximum amount of force before breakage was measured in Newtons. The implant was then turned 180 degrees, and the test was repeated on the other side of the implant. Thus, two tests were available for each implant.

The results of the testing indicated statistically significant differences (95% confidence level) between the mean values of the control groups and each of the corresponding test groups. The mean values of each of the Osseotite® titanium alloy 6AL-4V ELI implants test groups (light, medium, and heavy coverage) required 10.8N (n=23, standard deviation=5.32), 14.1N (n=24, standard deviation=5.98), and 12.8N (n=23, standard deviation=4.78) of force, respectively, to break away the bone from the implant. The mean values of the Osseotite® CP titanium test groups (light, medium, heavy coverage) required 8.2N (n=24, standard deviation=4.21), 10.5N (n=24, standard deviation=4.38), and 11.6N (n=24, standard deviation=4.89) more force, respectively, to break away the bone from the implant. The mean values of each of the Osseotite® titanium alloy 6AL-4V ELI implants test groups (light, medium, and heavy coverage) required 157%, 235%, and 204% more force, respectively, to break away the bone from the implant than that of the corresponding control group. The mean values of the Osseotite® CP titanium test groups (light, medium, heavy coverage) required 901%, 1178%, and 1319% more force, respectively, to break away the bone from the implant than the corresponding control group. Thus, any amount of HA nanocrystal coverage (i.e., light, medium, and heavy) was shown to be beneficial to the performance of the implants, and the implants having medium and heavy HA nanocrystal depositions were found to have slightly better performance than those having light deposition.

The previous embodiments describe surfaces that have received nanoparticles of HA. In an alternative embodiment, prior to depositing discrete nanoparticles (e.g., HA nanocrystals) on the implant surface, the surface is treated to form controllable, generally permanent nanostructures. The nanostructures may be formed directly on the implant surface. Preferably, however, the implant surface is treated to first form microstructures and then form nanostructures. The microstructures may be formed using any suitable technique including, but not limited to, those described in detail in U.S. Pat. No. 5,876,453 entitled "Implant Surface Preparation," U.S. Pat. App. Pub. No. 2004/0265780 entitled "Surface Treatment Process for Implants Made of Titanium Alloy," and U.S. Pat. App. Pub. No. 2006/0219661 entitled "Surface Treatment Methods for Implants Made of Titanium or Titanium Alloy," all of which are incorporated by reference in their entirety.

Controllable, generally permanent nanostructures are then applied to the implant surface prior to depositing the discrete nanoparticles on the implant surface. The controllable permanent nanostructures may be applied using techniques described in PCT/US2006/010281, entitled "Controllable Nanostructuring On Micro-Structured Surfaces," which is incorporated by reference in its entirety. The nanostructures are formed by depositing a vapor of nanostructuring material on the implant surface and forming nanostructures from the nanostructuring material. The nanostructuring material may be vaporized using, for example, evaporation, sputtering, and chemical vapor deposition. Exemplary methods of deposition include, but are not limited to, sputter coating, thermal vapor coating, plasma spraying, electron-beam physical vapor deposition (EB-PVD) technology, chemical vapor deposition technology, ion plating, and combinations thereof. The generally permanent nanostructures may also be created using subtractive methods including, but not limited to, chemical etching or electrochemical etching techniques. The nanostructures are composed of a material similar to the base implant material (e.g., titanium) and are, thus, assumed to be generally permanent and minimally bio-reactive. The nanostructures are melted into the implant surface and typically have minimal undercuts and a less complex geometry than the HA nanocrystals described above.

A secondary nanotopography may then be applied to the implant surface utilizing biochemically active nanoparticles (e.g., HA nanocrystals) described above. The combination of microstructures, generally permanent nanostructures, and biochemically active nanoparticles (e.g., HA nanocrystals) can be useful in increasing the rate and/or extent of bone-to-implant integration.

Depending on the amount of nanostructures formed on the surface of the implant, the secondary nanotopography may be deposited on the nanostructures or on a generally flat part of the implant surface (e.g., between nanostructures). For example, if many nanostructures have been formed on the implant surface, a greater amount of nanoparticles may be located on the nanostructures themselves. However, if fewer nanostructures are formed, fewer nanoparticles will be deposited on the nanostructures, and a greater amount of nanoparticles will be deposited on the generally flat part of the implant part of the implant surface.

In this alternative embodiment of applying nanoparticles to a generally permanent nanostructural surface, the nanoparticles of calcium phosphate preferably directly bond to a titanium oxide and/or titanium hydroxide layer formed on the surface of the implant. Thus, the methods of the present invention do not require an intermediary molecule (e.g., an alkoxide or tri-functional silanes such as aminopropyltriethoxysilane) to bond the nanoparticles to the implant. The intermediary molecule may, however, be applied. Rather, the nanoparticles are deposited using a one-step process of exposing the roughened surface of the implant to a colloidal solution including the nanoparticles.

While the present invention has been generally described relative to the part of the implant contacting bone tissue, it is contemplated that the acts etching, acid etching, roughening, and depositing herein described may be performed on the entire implant.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. A method of forming an implant to be implanted into living bone, the method comprising the acts of:
   forming a microscale roughened surface on at least a portion of the implant surface;
   forming a first nanotopography on the microscale roughened surface; and
   depositing a second nanotopography on portions of the first nanotopography, wherein a portion of the first nanotopography is exposed through the second nanotopography such that the exposed portion of the first nanotopography is for contacting bone.

2. The method of claim 1, wherein the implant is made of a metal comprising tantalum, cobalt, chromium, titanium, stainless steel, or alloys thereof.

3. The method of claim 1, wherein the implant is a dental implant.

4. The method of claim 1, wherein the first nanotopography includes a nanoscale roughened surface.

5. The method of claim 1, wherein the first nanotopography includes generally permanent nanostructures.

6. The method of claim 1, wherein the second nanotopography includes discrete nanoparticles comprising a material having a property that promotes osseointegration.

7. The method of claim 6, wherein the discrete nanoparticles include hydroxyapatite nanoparticles.

8. The method of claim 7, wherein the discrete hydroxyapatite nanoparticles are deposited by exposing the implant to a solution including the hydroxyapatite nanoparticles.

9. The method of claim 8, wherein the solution further includes a 2-methoxyethanol solvent.

10. The method of claim 1, wherein the act of forming a microscale roughened surface includes grist blasting.

11. A method of forming an implant, the method comprising:
   forming controllable, generally permanent nanostructures on at least a portion of the implant; and depositing discrete nanoparticles on or between at least some of the generally permanent nanostructures, wherein a portion of the generally permanent nanostructures is exposed between at least some of the discrete nanoparticles such that the exposed portion between the discrete nanoparticles is for contacting bone.

12. The method of claim 11, wherein the generally permanent nanostructures are applied to a portion of the implant including a microscale topography.

13. The method of claim 11, wherein the discrete nanoparticles include hydroxyapatite nanocrystals.

14. The method of claim 13, wherein the act of depositing discrete nanoparticles includes exposing the implant to a solution including the hydroxyapatite nanocrystals.

15. The method of claim 14, wherein the solution further includes a 2-methoxyethanol solvent.

16. The method of claim 11, wherein the implant is made of a metal comprising at least one tantalum, cobalt, chromium, titanium, stainless steel, or alloys thereof.

17. The method of claim 11, wherein the implant is a dental implant.

18. The method of claim 11 further comprising, prior to forming the generally permanent nanostructures, forming a microscale surface topography on at least a portion of the implant.

19. The method of claim 18, wherein the act of forming microscale surface topography includes grist blasting.

\* \* \* \* \*